(12) United States Patent
Cheng et al.

(10) Patent No.: US 11,666,224 B2
(45) Date of Patent: Jun. 6, 2023

(54) INTRAOPERATIVE OPTOACOUSTIC GUIDE APPARATUS AND METHOD

(71) Applicant: Purdue Research Foundation, West Lafayette, IN (US)

(72) Inventors: Ji-xin Cheng, West Lafeyette, IN (US); Pu Wang, Suzhou (CN); Lu Lan, Suzhou (CN); Yan Xia, West Lafayette, IN (US); Ke Huo, West Lafayette, IN (US)

(73) Assignee: PURDUE RESEARCH FOUNDATION, West Lafayette, IN (US)

( * ) Notice: Subject to any disclaimer, the term of this patent is extended or adjusted under 35 U.S.C. 154(b) by 199 days.

(21) Appl. No.: 15/774,070

(22) PCT Filed: Nov. 7, 2016

(86) PCT No.: PCT/US2016/060798
§ 371 (c)(1),
(2) Date: May 7, 2018

(87) PCT Pub. No.: WO2017/079732
PCT Pub. Date: May 11, 2017

(65) Prior Publication Data
US 2018/0310831 A1 Nov. 1, 2018

Related U.S. Application Data

(60) Provisional application No. 62/295,028, filed on Feb. 13, 2016, provisional application No. 62/252,486, filed on Nov. 7, 2015.

(51) Int. Cl.
*A61B 5/00* (2006.01)
*A61B 90/00* (2016.01)
(Continued)

(52) U.S. Cl.
CPC ............ *A61B 5/0095* (2013.01); *A61B 5/061* (2013.01); *A61B 5/4836* (2013.01);
(Continued)

(58) Field of Classification Search
CPC ....... A61B 5/0095; A61B 5/061; A61B 34/20; A61B 2034/2046; A61B 90/36;
(Continued)

(56) References Cited

U.S. PATENT DOCUMENTS

2004/0015053 A1* 1/2004 Bieger ............... A61B 1/00149
600/117
2004/0131299 A1* 7/2004 Adoram ............... A61B 5/0095
385/12
(Continued)

FOREIGN PATENT DOCUMENTS

RU 2243630 C2 * 12/2004 ............. G21K 1/006

OTHER PUBLICATIONS

Zou et al.; Broadband miniature fiber optic ultrasound generator; published on Jul. 18, 2014; Optics Express; vol. 22, Issue 15, pp. 18119-18127 (Year: 2014).*

(Continued)

*Primary Examiner* — Chao Sheng
(74) *Attorney, Agent, or Firm* — Gutwein Law; Tyler B. Droste

(57) ABSTRACT

A lesion detection system for use with a patient, comprising an optoacoustic guide wire assembly configured to be insertable into a patient's tissue. The optical acoustic guide wire assembly can be comprised of an optical waveguide have a first end and a second end, a light source coupled to the second end of the optical waveguide, wherein said light source configured to emit energy to the patient's tissue, at least one transducer configured to detect an ultrasound (Continued)

signal emitted from the patient's tissue in response to energy emitted from the light source, and a computer system.

22 Claims, 14 Drawing Sheets

(51) Int. Cl.

| | | |
|---|---|---|
| A61B 5/06 | (2006.01) | |
| A61B 34/20 | (2016.01) | |
| A61B 17/32 | (2006.01) | |
| A61B 17/3205 | (2006.01) | |
| A61B 17/50 | (2006.01) | |
| A61B 8/08 | (2006.01) | |
| A61B 90/30 | (2016.01) | |
| A61B 90/50 | (2016.01) | |
| A61B 17/00 | (2006.01) | |
| G01N 33/48 | (2006.01) | |

(52) U.S. Cl.
CPC ............ *A61B 5/6851* (2013.01); *A61B 5/743* (2013.01); *A61B 17/3205* (2013.01); *A61B 17/320016* (2013.01); *A61B 34/20* (2016.02); *A61B 90/36* (2016.02); *A61B 90/37* (2016.02); *G01N 33/48* (2013.01); *A61B 5/064* (2013.01); *A61B 5/7445* (2013.01); *A61B 8/0825* (2013.01); *A61B 17/50* (2013.01); *A61B 2017/008* (2013.01); *A61B 2017/00707* (2013.01); *A61B 2034/2057* (2016.02); *A61B 2090/306* (2016.02); *A61B 2090/365* (2016.02); *A61B 2090/378* (2016.02); *A61B 2090/502* (2016.02)

(58) Field of Classification Search
CPC .............. A61B 90/37; A61B 2090/306; A61B 2090/365; A61B 2090/378; A61B 2090/502; A61B 5/4836; A61B 5/6851; A61B 5/064; A61B 5/7445; A61B 17/320016; A61B 17/3205; A61B 17/50; A61B 2017/00707; A61B 2017/008; A61B 2034/2057; A61B 8/0825; G01N 33/45

See application file for complete search history.

(56) References Cited

U.S. PATENT DOCUMENTS

| | | | |
|---|---|---|---|
| 2004/0184154 A1* | 9/2004 | Ito | G02B 5/0226 359/599 |
| 2005/0131289 A1* | 6/2005 | Aharoni | A61B 8/12 600/407 |
| 2005/0203375 A1* | 9/2005 | Willis | A61B 8/445 600/407 |
| 2005/0277913 A1* | 12/2005 | McCary | A61B 90/36 606/1 |
| 2010/0168561 A1* | 7/2010 | Anderson | A61B 90/36 600/424 |
| 2013/0237811 A1* | 9/2013 | Mihailescu | A61B 90/361 600/424 |

OTHER PUBLICATIONS

Chang et al.; Candle soot nanoparticles-polydimethylsiloxane composites for laser ultrasound transducers; published on Oct. 23, 2015; Applied Physics Letters; vol. 107, Issue 16; 161903 p. 1-5 (Year: 2015).*

Wu et al.; High-efficiency optical ultrasound generation using one-pot synthesized polydimethylsiloxane-gold nanoparticle nanocomposite; published on Jul. 18, 2012; Journal of the Optical Society of America B; vol. 29, Issue 8; pp. 2016-2020 (Year: 2012).*

Baac et al., Evaluation of optoacoustic conversion efficiency of light-absorbing films for optoacoustic transmitter applications; Proceedings of SPIE; vol. 7899, Photons Plus Ultrasound: Imaging and Sensing 2011; 789940 (2011) (Year: 2011).*

* cited by examiner

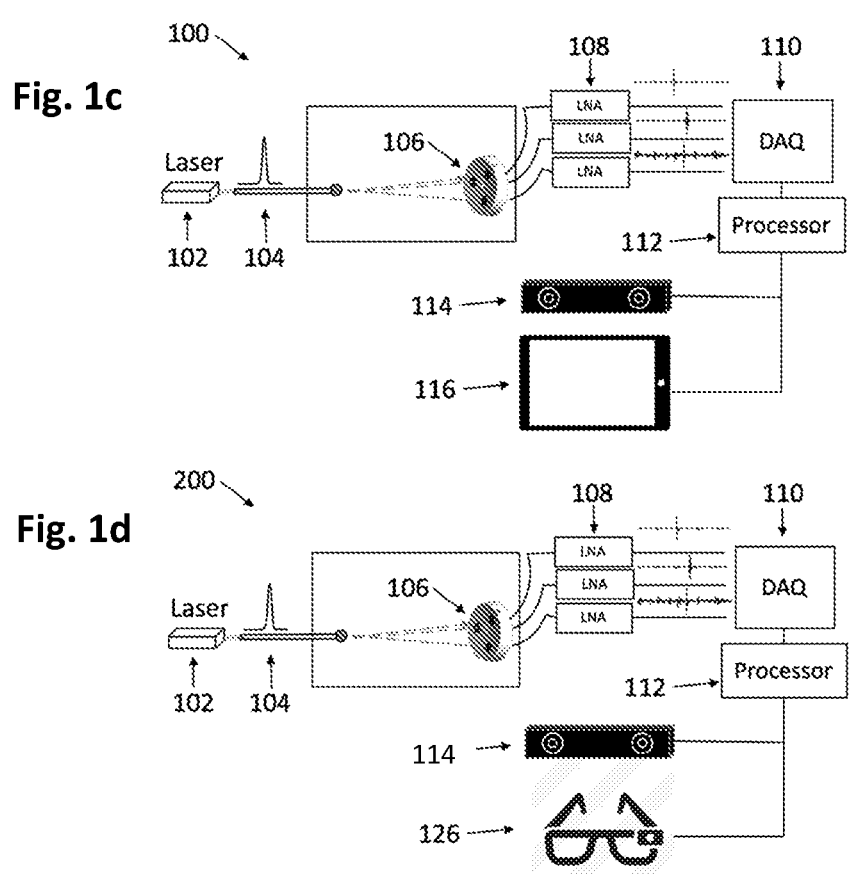

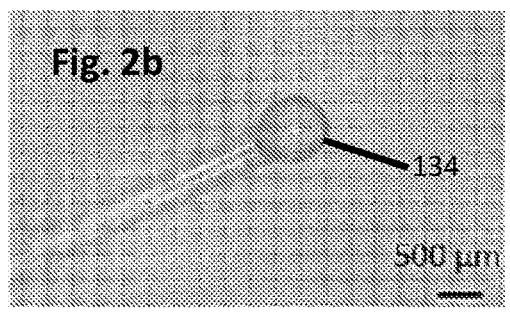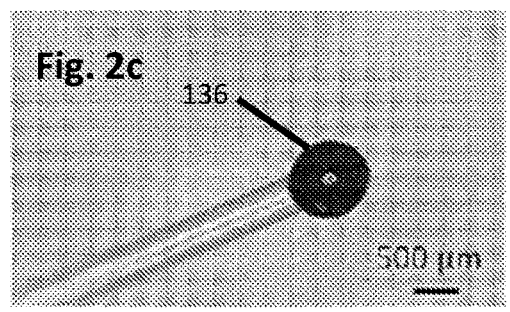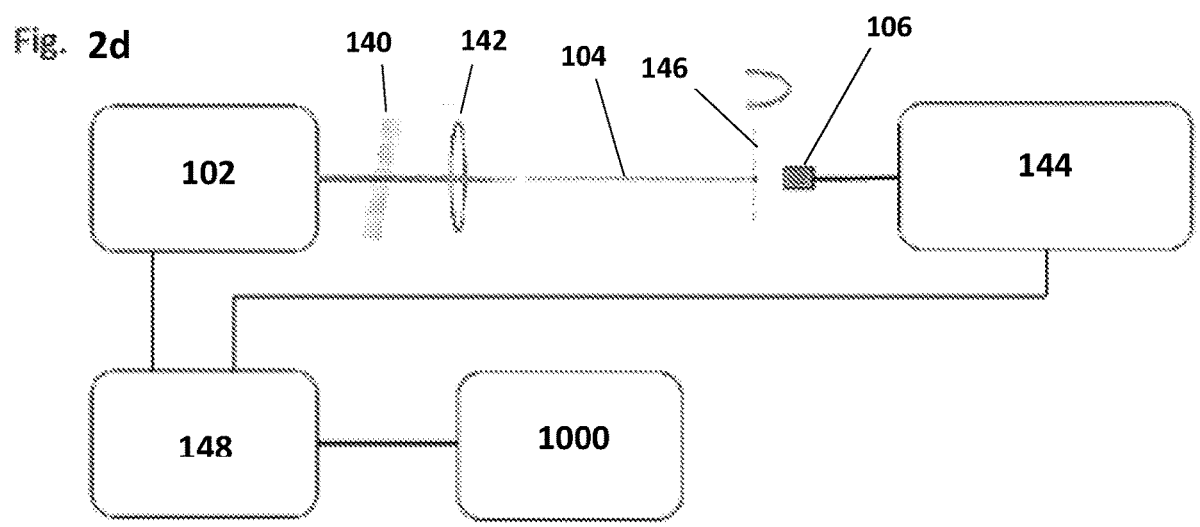

INTRAOPERATIVE OPTOACOUSTIC GUIDE APPARATUS AND METHOD

CROSS-REFERENCE TO RELATED APPLICATION

This U.S. patent application claims priority to U.S. Provisional Application 62/252,486 filed Nov. 7, 2015 and U.S. Provisional Application 62/295,028 filed on Feb. 13, 2016, the disclosure of which is considered part of the disclosure of this application and is hereby incorporated by reference in its entirety.

FIELD OF THE INVENTION

The present application relates to optical detection systems and in particular to a photoacoustic detection system that can be used in surgical or medical operations.

BACKGROUND

This section introduces aspects that may help facilitate a better understanding of the disclosure. Accordingly, these statements are to be read in this light and are not to be understood as admissions about what is or is not prior art.

Locating an implanted device, needle biopsy device, punctuation device, or lesion that is planned to be removed during a surgical procedure is a critical issue. As an example, 33%-50% of all breast cancer diagnosed are non-palpable, and the management of these non-palpable breast cancers poses a unique challenge for surgeons because an accurate localization of non-palpable cancer is essential to achieve clear surgical margins for good surgical outcome.

Current methods are incapable of providing quantitative location of the implanted device or real-time visual feedback of that location. Therefore, it creates problems on a large re-excision rate, and a prolonged surgical time. These factors subsequently result in higher surgical cost/waste, high risk of complication, and physical pain and emotional distress for the patients. Thus, there is an unmet need for an effective surgical arrangement that can guide lesion excision during an operation, and also provides suggestive information on margin status to help reduce the re-operation rate.

As another example, during an endobronchial ultrasound guided needle biopsy, the doctors may have a hard time to control the biopsy needle to accurately sample the location of interest, which may create a large false negative biopsy rate. Therefore, an accurate and intuitive method to locate such device or lesion is critical for reducing procedure time and increase the procedure accuracy.

BRIEF SUMMARY OF THE INVENTION

In one aspect, this disclosure is related to a surgical localization system for use with a patient, comprising an optoacoustic guide wire assembly configured to be insertable into a patient's tissue. The optical acoustic guide wire assembly can be comprised of an optical waveguide having a first end and a second end, a light source coupled to the second end of the optical waveguide, wherein said light source is configured to emit energy to the patient's tissue, at least one transducer or a combination of transducer arrays configured to detect an ultrasound signal emitted from the patient's tissue in response to energy emitted from the light source, and a computer system.

In another aspect, this disclosure is related to a method for determining the location of a lesion within a patient tissue, comprising photoacoustically stimulating the absorber with a laser source beam capable of generating photoacoustic waves via an optoacoustic guide wire assembly configured to be insertable into a patient's tissue. The optoacoustic guide wire assembly can comprise an optical waveguide having a first end and a second end, a diffuser formed at the first end of the optical waveguide, and an absorber layer formed on said diffuser. At least one transducer can be positioned proximate to said optoacoustic guide wire assembly, wherein said transducer configured to detect an optoacoustic waveform. The optoacoustic waveform emitted can be detected by the optoacoustic guide wire from the tissue. The detected optoacoustic waveform can then be applied via an algorithm. A coordinate can then be generated to identify the location of a lesion within the patient tissue.

In another aspect, this disclosure is related to a method for determining the location of an implantable or insertable device (i.e. biopsy needle) within a patient tissue, comprising photoacoustically stimulating the absorber on the distal end of the optical waveguide with a laser source beam capable of generating photoacoustic waves via an optoacoustic guide wire assembly integrated with the implantable or insertable device to be implantable or insertable into a patient's tissue. The optoacoustic guide wire assembly can comprise an optical waveguide having a first end and a second end, a diffuser formed at the first end of the optical waveguide, and an absorber layer formed on said diffuser. The assembly is integrated to the implantable or insertable device. At least one transducer can be positioned proximate to said optoacoustic guide wire assembly, wherein said transducer is configured to detect an optoacoustic waveform. The optoacoustic waveform emitted can be detected by the optoacoustic guide wire from the tissue. The detected optoacoustic waveform can then be applied via an algorithm. A coordinate can then be generated to identify the location of an implantable or insertable device within the patient's tissue.

In yet another aspect, this disclosure is related to a lesion detection and excision system for a patient, comprising an optoacoustic guide wire assembly, a light source coupled to the second end of the optical waveguide, wherein said light source emits energy to optical absorbers on the distal end of the optical waveguide through the diffuser at the first end of the optical waveguide, a surgical instrument having at least one transducer configured to detect an ultrasound signal emitted from the patient's tissue in response to activation from the light source, and a computer system, wherein the computer system is configured to coordinate activation of the light source and acquisition of the ultrasound signal in order to generate a proximity signal between position of the first end of the optoacoustic guide wire assembly and the surgical instrument. The optoacoustic guide wire assembly can be comprised of an optical waveguide have a first end and a second end, a diffuser formed at the first end of the optical waveguide, and an absorber layer formed on said diffuser, wherein said optoacoustic guide wire assembly is configured to be insertable into a patient's tissue.

The system can further include an augmented reality image system comprising a camera to capture a real image of the patient's tissue or a see-through glass, and a display to display an augmented reality image. The computer system of the lesion detection and excision system can be further configured to control the capture of a real image of the patient, analyze the virtual images and proximity signal to estimate a position and gaze direction of the camera using the optoacoustic guide wire assembly and the transducer, and generate an augmented reality image by overlaying a region of the virtual image corresponding to the estimated position and gaze direction of the camera over the real image.

BRIEF DESCRIPTION OF THE DRAWINGS

The features and advantages of this disclosure, and the manner of attaining them, will be more apparent and better understood by reference to the following descriptions of the disclosed system and process, taken in conjunction with the accompanying drawings, wherein:

FIG. 1c is an illustration of an exemplary embodiment of an optoacoustic guide system for precise surgery or device localization with augmented reality.

FIG. 1d is an illustration of an exemplary embodiment of an optoacoustic guide wire system for precise surgery or device localization with augmented reality.

FIG. 2b is an illustration of an exemplary embodiment of an optoacoustic guide wire with a diffusion sphere.

FIG. 2c is an illustration of an exemplary embodiment of an optoacoustic guide wire with a graphite layer on top of a diffusion sphere.

FIG. 2d is a schematic of an exemplary embodiment for a characterization setup for light intensity directivity map and optoacoustic signal intensity.

DETAILED DESCRIPTION OF THE INVENTION

Figure 1A:
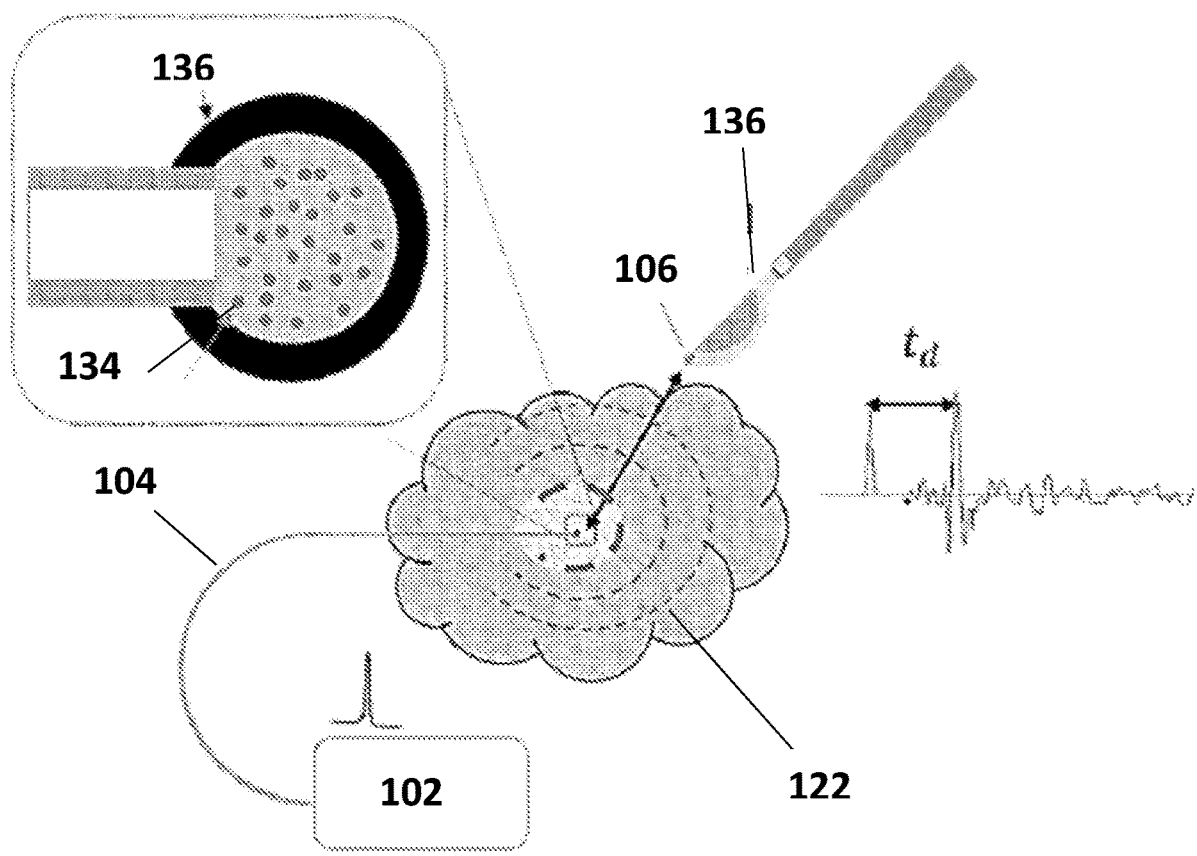
FIG. 1a is an illustration of an exemplary embodiment optoacoustic guide wire system for precise surgery.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

A novel surgical arrangement that could guide lesion, tumor, or other excision during a surgical operation, such as breast-conserving surgery (BCS) or other similar surgical procedure, and also provides suggestive information on margin status to help reduce the re-operation rate is disclosed herein. Lack of accurate real-time surgical guidance to locate the exact cancerous area and confirm excision of sufficient margins is a critical factor for current high re-operation rate. According to the present disclosure, a fiber-delivered optoacoustic guide wire assembly which mimics the traditional wire localization but provides addition real-time quantitative information of the location of the lesion site in operation is utilized.

In one exemplary embodiment, a nano-composite sphere of zinc-oxide (ZnO) nanoparticles (less than about 100 nm) and epoxy is formed on the proximal end of a multimode optical waveguide to diffuse light. In one exemplary embodiment, the optical waveguide can be an optical fiber. Alternatively, the epoxy can be replaced with any suitable material of higher thermal expansion, such as polydimethylsiloxane (PDMS) or silicone. The composite can then be coated by an optical absorber 136, to transfer the light into an omnidirectional optoacoustic source when excited by pulsed laser. The optical absorber 136 can be graphite, graphene or carbon nanotubes which mixes with epoxy or other material of higher thermal expansion such as polydimethylsiloxane (PDMS) or silicone. The optoacoustic signal generated can have a high dynamic range of about 50 dB and can spread in a large apex angle of about 260 degrees. In an exemplary embodiment, by integrating ultrasound transducer detector 106 into a surgical blade and using real-time visual guidance software, the novel optoacoustic surgical arrangement with the guide wire is capable of providing real-time lesion removal guide and improve the excision accuracy and efficiency.

A fiber-delivered optoacoustic guide wire assembly 104 is utilized in the surgical arrangement according to the present disclosure. This guide wire assembly 104 is not only able to provide both real-time surgical guidance and quantitative distance information of lesion site to surgeons during the operation, but also allows intuitive cutting procedure to surgeons by integrating a miniaturized ultrasound transducer to a surgical equipment. Referring to FIG. 1a, a schematics presentation of an optoacoustic guide arrangement system 100 for precise excision of tissue.

As shown in FIG. 1a, a nanocomposite sphere to act as a diffuser 134 can be formed on the proximal end of a multimode optical waveguide 132, which can enable light diffusion within a large apex angle of about 260 degrees. The sphere can have an outer coating to form an optical absorber 136 and which has a high optical absorption and high thermal expansion, transforms light energy into high-amplitude ultrasound signal upon pulsed laser irradiation at the distal end of optical waveguide 132. Therefore, an omnidirectional optoacoustic source can be generated inside lesion site of the tissue 122, when the guide is inserted into the lesion center before surgery.

In an exemplary embodiment, by measuring the time delay between the laser pulse and optoacoustic pulse picked up by at least one transducer 106 on a surgical instrument, such as a scalpel 124, quantitative distance information of the scalpel 124 with regard to the optoacoustic guide wire assembly 104 are obtained. Such distance information are used to provide real-time surgical guidance of lesion excision to surgeons in operation, and help improve lesion excision efficiency. Additionally, if the appropriate lesion three-dimensional profile is previously known, suggestive information about the margin status are determined and thus could potentially help reduce the re-operation rates.

In experiments, the optoacoustic signal acquired demonstrates more than about 30 dB signal-to-noise ratio (SNR) after passing through chicken breast of about 10 cm thickness. Such high SNR after 10 cm propagation distance is sufficient to accommodate the detection distance need in real clinic practice. Furthermore, the optoacoustic guide wire according to the present disclosure is fabricated based on cost-effective methods and is naturally compatible with a commercial ultrasound system currently used in BCS.

As a design parameter, the optoacoustic signal generated by the optoacoustic guide should be able to be detected across a wide angular range and over a large distance range. Because the amplitude of optoacoustic signal generated is proportional to the incident pulse power, this demands the light distribution on absorber 136 layer to cover a wide angular range. For an optical waveguide, the angular range of light illumination is limited by its numerical aperture (NA). In one exemplary embodiment, an optical waveguide with about 0.22 NA can only spread light within the apex angle of about 25.4° in air.

To enable the wide angular light emission, the diffuser 134 sphere shown in FIG. 1a is provided according to the present disclosure on the tip of fiber using nanoparticles and epoxy composite. The size of the nanoparticles was chosen to be sufficiently small when compared to the laser wavelength, can enable Raleigh scattering by these nanoparticles and scrambling the incident light in randomized directions. In one exemplary embodiment the nanoparticles can be ZnO nanoparticles. Consequently, a relatively uniform distributed angular light emission is produced at the tip of the optical waveguide 132. According to one embodiment, a polished fiber tip is submerged about 100 μm below the solution surface in a ZnO and epoxy solution with a concentration about 15% in solution, pulled out quickly and cured in room temperature to fabricate the diffuser sphere.

In surgery, lesion or tissue excision is performed at arbitrary position and angle with regard to the tumor site. Therefore, the optoacoustic signal generated by the optoacoustic emitter should be detected across a wide angular range and over a large distance range. The initial pressure generated by the pulsed laser excitation can be written as $$P_0 = \frac{\beta}{\kappa \rho C_v} \eta_{th} \mu_a F$$

where β is the thermal expansion coefficient, κ is the isothermal compressibility, $C_v$ is the specific heat capacity, $\eta\_th$ is the heat conversion efficiency, $\mu\_a$ is the optical absorption coefficient, and F is the optical fluence. To make the optoacoustic emitter detected in all directions and over a large distance range, it is configured in two main perspectives.

The distribution of light fluence, F, on the outer absorption layer 136 needs to cover a wide angular range to enable a wide angular generation of optoacoustic signal. One exemplary embodiment of the present invention has a diffuser sphere 134 on the tip of fiber using ZnO nanoparticles and epoxy composite to enable a wide angular light emission. The ZnO nanoparticles had a diameter of about 100 nm, which is much smaller than the laser wavelength, thus enabling the Raleigh scattering in all directions. The incident light would be scrambled in randomized directions, and a relatively uniform distributed angular light emission is produced at the fiber tip of the optical waveguide 132.

The intensity of initial optoacoustic signal needs to be strong enough to make the ultrasound signal detectable over a large distance range. Therefore, materials with high optical absorption coefficient $\mu_a$, heat conversion efficiency $\eta_{th}$ and thermal expansion coefficient 6 need to be applied as the outer absorption layer 136 to transform light into large amplitude ultrasound. In one embodiment, a graphite and epoxy mixture can be used for the outer absorption layer 136 on the diffuser sphere 134, because graphite has high optical absorption and heat transduction, and epoxy is readily-available and has a three times higher thermal expansion coefficient than gold.

Figure 1B:
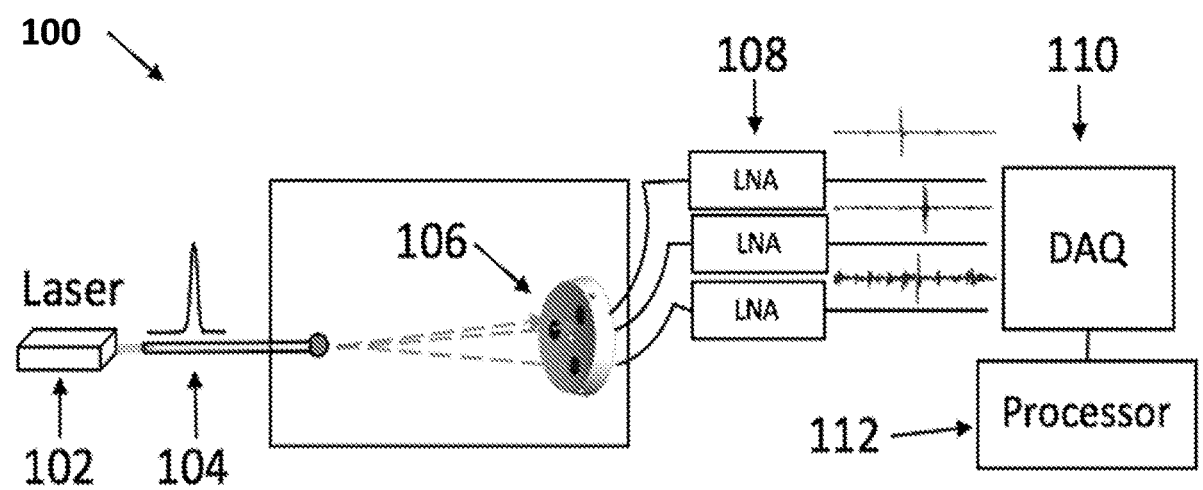
FIG. 1b is an illustration of an exemplary embodiment of an optoacoustic guide wire localization system.

FIG. 1b is an illustration of another exemplary embodiment of an optoacoustic guide wire localization system 100. The system 100 can include a tunable pulse laser 102, an optoacoustic guide wire assembly 104, an ultrasound transducer group 106, a low noise amplifier (LNA) group 108, a data acquisition (DAQ) unit 110, a central processor 112. The pulsed laser can have a pulse duration from about 100 fs to about 5 us and repetition rate from about 1 Hz to about 20 KHz. Applying the trilateration concept, a customized ultrasound transducer group 106 is developed to achieve spatial localization of the tip of the optoacoustic guide wire assembly 104 by measuring the distances between each transducer 106 and the tip of the optoacoustic guide wire assembly 104.

The time-of-flight (TOF) acoustic signals acquired by the transducers 106 are amplified by the LNA group 108, digitized by the DAQ unit 110 and sent to the central processor 112. In one exemplary embodiment, each transducer 106 can have an independently associated LNA 108. The distance between the tip of the guide wire assembly 104 and each ultrasound transducer is calculated based on the TOF acoustic signals. The processor 112 can perform various functions and it is contemplated that more than one processor 112 can be employed within the system 100.

Some of the functions performed by the processor 112 include receiving data, signal peak detection, TOF calculation, signal synchronization, spatial trilateration algorithm, optical tracking algorithm, spatial geometry calculation, data streaming and command control of the system 100. The data source for processor 112 include but is not limited to the acoustic signals from the transducer group 106, optical tracking data from stereo camera 114 and hardware and software information from tablet 116. The trilateration, tracking and other algorithms are executable code stored in processor 112 and various algorithms of each function are employed in the present invention. The data transfer and streaming media to and from processor 112 include but is not limited to Peripheral Component Interconnect Express (PCIe), universal serial bus (USB) wire and local area network (LAN). The processor 112 can be more than one computing device, or a single computing device with more than one microprocessor. The processor 112 is a stand-alone computing system with internal or external memory, a microprocessor and additional standard computing features. The processor 112 can be selected from the group comprising a PC, laptop computer, microprocessor, or alternative computing apparatus or system.

In one exemplary embodiment, the ultrasound transducer group 106 can comprise three 5 MHz ultrasound transducers separated from each other at about 3 cm. The pulsed laser from the laser 102 is diffused by a ball-shape optical diffuser 134 and absorbed by an optical absorber layer 136 coated outside of the ball-shape diffuser 134. In one embodiment the pulsed laser 102 can be a 2 ns laser. The absorber layer 136 can undergo a thermal expansion and therefore creates wideband ultrasonic waves, which are often referred to as photoacoustic waves. The three ultrasound transducers within the transducer group 106 can simultaneously detect the photoacoustic waves generated at the tip of the guide wire assembly 104. The recorded TOF acoustic signals are amplified by the LNA group 108, digitized by the DAQ unit 110 (PCI DAQ board, 3 IO channel, 75 Mega Samples/s) and sent to the processor 112 for processing. Then the relative location of the tip of the guide wire assembly 104 is obtained through trilateration based on the TOF acoustic signals. Considering that the detected photoacoustic signals are MHz acoustic waves, sub-millimeter detection accuracy of the tip of the guide wire assembly 104 is achieved.

An about 2 mega pascals (MPa) acoustic wave can be generated and a SNR of about 53 dB can be achieved at about 106 mm distance away from the transducer under an excitation laser energy of about 0.55 mJ from laser 102 at the distal end of the guide wire assembly 104. Considering an ultrasound attenuation of about 2.5 dB/cm at about 5 MHz in fat tissue, the SNR was still at least about 28 dB after passing through about 10 cm tissue. At the same time, the feedback rate determined by the repetition rate of the laser 102 is about 20 Hz. By comparing the measured shift based on localization result against physical shift, the localization of the tip of the guide wire 104 by using the transducer group 106 demonstrates a mean error of about 0.15 mm, which is much smaller than the size of the guide wire tip (about 600 μm).

FIG. 1c is an illustration of an exemplary embodiment of an optoacoustic guide system 100 for precise surgery or device localization with augmented reality concept. The system 100 includes a tunable pulse laser 102, an optoacoustic guide wire assembly 104, an ultrasound transducer group 106, a low noise amplifier (LNA) group 108, a data acquisition (DAQ) unit 110, a central processor 112 and a combination of mounted stereo camera 114 and tablet 116. The system 100 can be used as a surgery guidance system or device localization system that incorporates acoustic localization, optical tracking and augmented reality.

The optoacoustic guide wire assembly 104 (see FIG. 2 for more detail) is inserted into a breast-mimicking phantom 118. Pulsed laser from the tunable pulse laser 102 passes through the fiber of the optoacoustic guide wire assembly 104 and excites omnidirectional MHz sound waves at the tip of the guide wire assembly 104. The sound waves from the tip of optoacoustic guide wire assembly 104 are detected by three ultrasound transducers on the transducer group 106 (see FIG. 5 for more detail) and used to quantify the distances between them and the tip of the guide wire assembly 104. Then the relative spatial location of the tip of the guide wire assembly 104 is solved using a customized trilateration algorithm. At the same time, infrared (IR) markers or a two-dimensional barcode fixed on the transducer group 106 reflect light from IR light source accompanied with the stereo camera 114. The IR marker group comprised of the IR markers is then detected and tracked by the stereo camera 114 with predefined spatial feature configuration. The IR marker group or two-dimensional barcode is a rigid body and forms a larger rigid body with the transducer group 106. So the pose and position of the transducer group 106 is obtained, combined with the spatial location of the tip of guide wire assembly 104 with respect to the transducer group, the spatial location of the tip of guide wire assembly 104 with respect to the tablet 116 is obtained. In the meantime, the camera on the tablet 116 catches a real-time view of the phantom 118. A lesion-like object is rendered and superimposed on the view of the tablet camera according to the spatial location of the tip of guide wire assembly 104. So both the view of the phantom 118 and the visualization of the tip of guide wire assembly 104 are displayed real-time on the screen of the tablet 116.

FIG. 1d illustrates another exemplary embodiment of an optoacoustic guide system 100 for precise surgery or device localization with augmented reality concept. The system 100 includes a tunable pulse laser 102, an optoacoustic guide wire assembly 104, an ultrasound transducer group 106, a low noise amplifier (LNA) group 108, a data acquisition (DAQ) unit 110, a central processor 112 and a combination of mounted stereo camera 124 and head-mounted display (HMD) 126. The optoacoustic guide wire localization sub-system in the system 100 is similar to that in system 100 as shown in FIG. 1a-c. The optical tracking and augmented reality display sub-system are replaced by stereo camera 124 mounted on a HMD 126. This provides a more intuitive guidance to the surgeon and even less inference to the normal surgical operations.

Figure 1E:
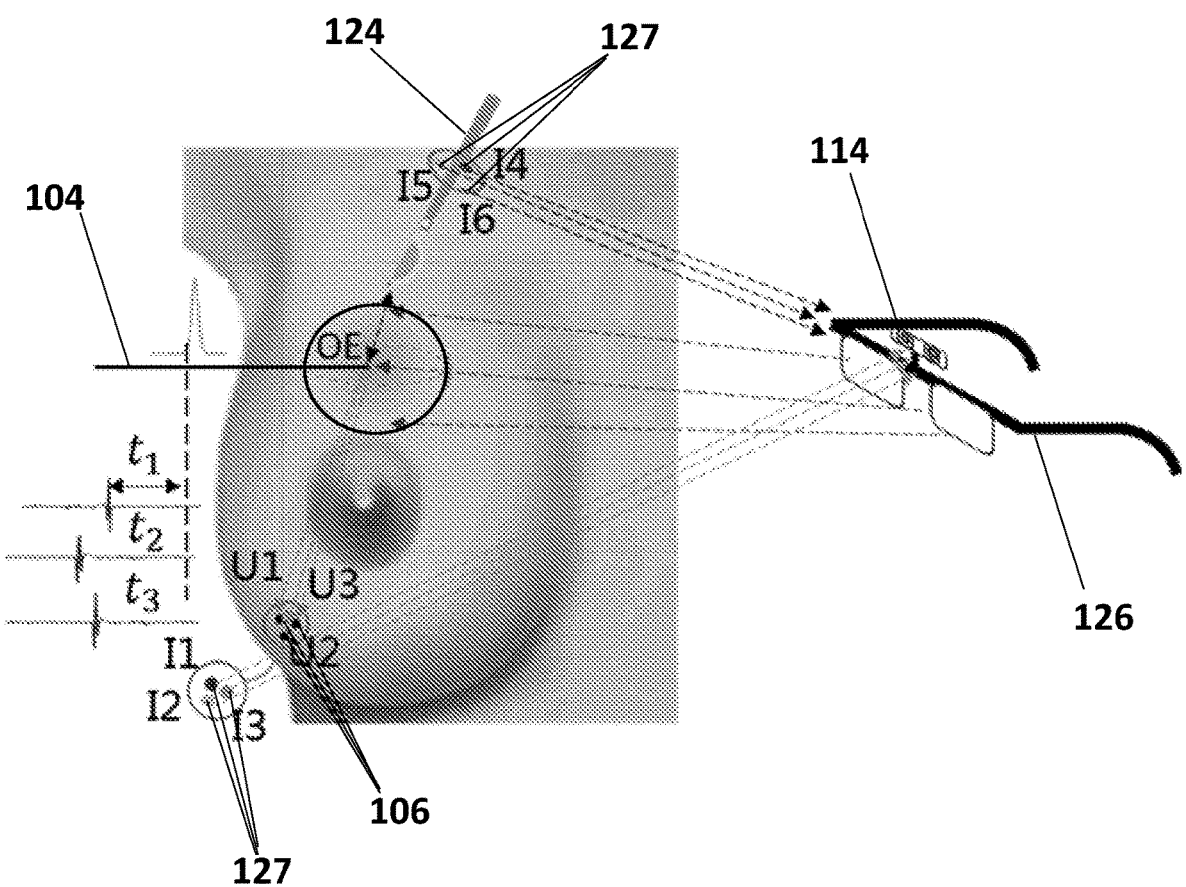
FIG. 1e is another illustration of an exemplary embodiment of an optoacoustic guide wire system for precise surgery or device localization with augmented reality.

Further FIG. 1e, further illustrates an exemplary embodiment of a system composed of an optoacoustic emitter (OE), such as an optoacoustic guide wire assembly 104, and head-mounted augmented reality system. A laser can be used to provide real-time quantitative information of the location of the tumor site intra operation. The optoacoustic guide wire assembly 104 can be preoperatively inserted into the breast tumor site under the guidance of mammography, ultrasound or MRI, and is configured to emit an acoustic pulse covering all solid angles when excited by external pulsed excitation source.

A group of ultrasound detectors 106 (U1, U2 and U3), which are attached to the targeted breast or tissue, could then detect the emitted acoustic pulse signal. The time delays of detected acoustic signal with regard to the excitation pulse would then be transferred to the distances d1, d2 and d3, where $d = v_s \cdot t$, where $v_s$ is the sound of speed inside breast tissue. With the distances of the optoacoustic emitter relative to the ultrasound detectors, localization of tumor with regard to the group of ultrasound detectors is known. A group of infrared (IR) I1-I3 markers 127 are attached within constraints of the patient tissue proximate to or to the group of ultrasound detectors. Furthermore, another group of IR markers 127 (I4-I6) can also be attached to the surgical instrument or scalpel 124, and can provide the relative position information of scalpel 124 with regard to tumor site 122. An augmented reality display device 126 wore by surgeon or held in front of the surgeon can be equipped with an IR pass stereo camera 114.

Then, using the images acquired by stereo camera 114, detection of the relative 6 degree of freedom (DOF) pose between those IR markers 127 and a display device 126 provides the relative position of transducer with regard to display device 126. By combining the relative position of optoacoustic guide wire assembly 104 to ultrasound detector group 106, and the ultrasound detector group 106 to display device 126, the relative position (3 DOF) of the optoacoustic emitter to display device 126 is obtained. Therefore, the localization of the optoacoustic emitter could then be visualized in the surgeon's view with the help of augmented reality images.

Then AR system can compute the relative position of six DOF between IR markers 127 and the display device. Also the communication unit on computer system can receive the 3D positional information of the optoacoustic guide wire assembly 104 with respect to transducer group 106. The computer 112 can estimate the optoacoustic guide wire assembly's 104 3D position relative to the display 126. The computer 112 can then generate an image representing the spatial profile of tumor and render this virtual tumor at the optoacoustic guide wire assembly's 104 position. This image can be generated from a pre-surgery CT or MRI. Furthermore, the computer 112 can retrieve a pre-built virtual model of the surgical knife 124 and overlay it on the image of the real knife according to the 6 DOF relative to the display 126. An indicator can be created and displayed on the display 126 as a quantitative hint for the surgeon. Based on the distance between the optoacoustic guide wire assembly 104 and surgical knife 124, a speaker can create an audible feedback during the surgery.

Additionally, if the dimension of the tumor is known, a virtual sphere 129 approximately the size of the tumor centered at the position of the optoacoustic guide wire assembly 104 can be rendered in surgeon's view, providing surgeons with intuitive visual perception of the tumor location and margin information. When the scalpel 124 gets inside the tumor site 122, a visual warning indicator can be displayed in the augmented reality display device 126 to alert the user. Additionally, a warning sound can also be provided.

This real-time visual perception of the tumor location and margin information, together with the distance of surgical blade to tumor as well as visual and sound indicators, could provide surgeon with real-time intuitive surgical guidance. Consequently, the excision efficiency and accuracy of tumor during the surgery is improved and the high re-operation rate of breast conserving surgery is reduced.

Figure 2A:
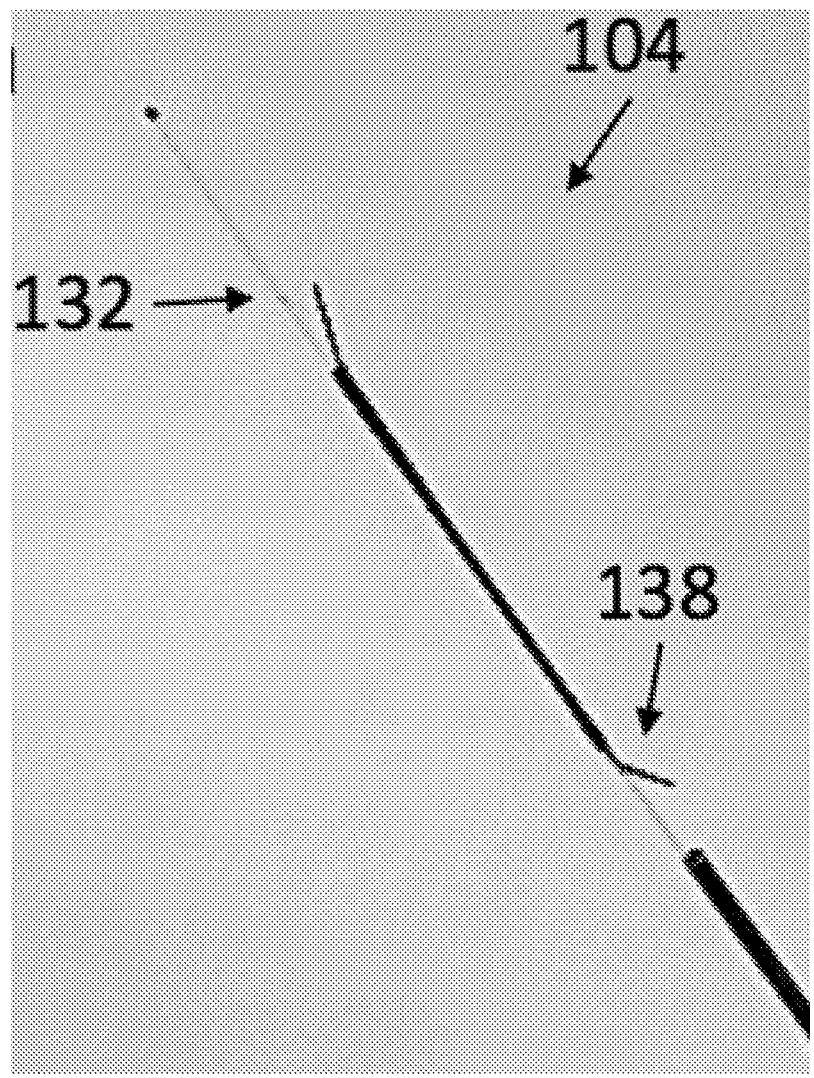
FIG. 2a is an illustration of an exemplary embodiment of an acoustic emitter on a hook guide wire.
Figure 3:
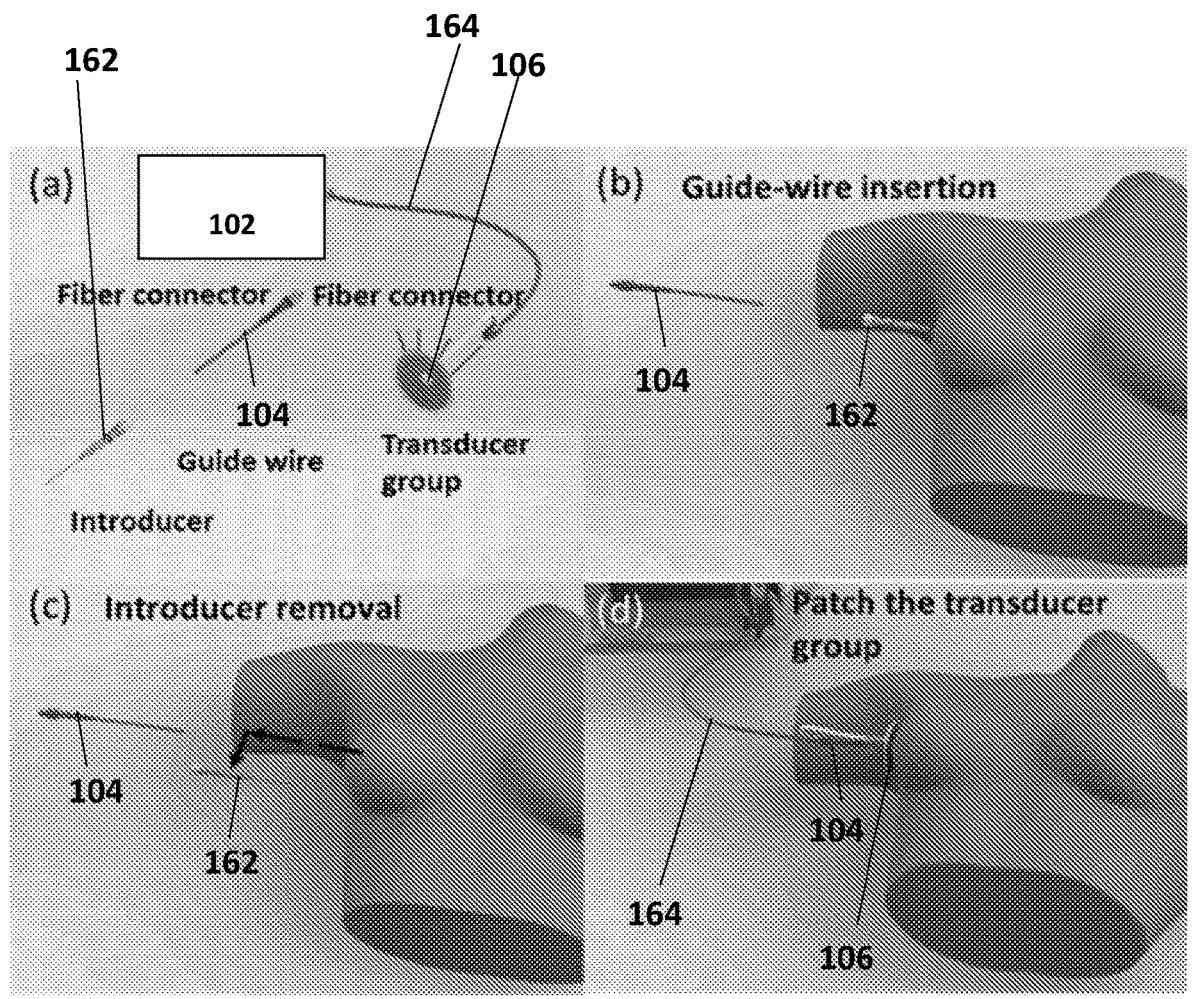
FIG. 3a is an illustration of exemplary parts comprising an optoacoustic guide wire and miniaturized ultrasound transducer group in accordance with at least one embodiment of the present invention.
FIG. 3b is an illustration of an exemplary procedure of inserting the optoacoustic guide wire and an exemplary embodiment of an opto-electrical interface on a transducer group to connect to the guide wire.
FIG. 3c is an illustration of an exemplary procedure of inserting the optoacoustic guide wire and an exemplary embodiment of an opto-electrical interface on a transducer group to connect to the guide wire.
FIG. 3d is an illustration of an exemplary procedure of inserting the optoacoustic guide wire and an exemplary embodiment of an opto-electrical interface on a transducer group to connect to the guide wire.

Referring to FIGS. 2a-2d, the steps in forming the optoacoustic guide wire and a setup on how to characterize the optoacoustic guide wire according to one embodiment is provided. As shown in FIG. 2a, an optoacoustic guide wire assembly 104 can have a sub-millimeter omnidirectional acoustic source with sufficient acoustic energy based on photoacoustic effect. The optoacoustic guide wire assembly 104 can include an optical waveguide 132, a ball shape optical diffuser 134 on the fiber tip, a layer of optical absorbers 136 outside the diffuser and an attached hook wire 138. Pulsed laser passes through the optical waveguide 132 and is diffused by the ball-shape diffuser 134 to all directions. The diffused laser will then be absorbed by the optical absorbers 136 coated outside of the ball-shape diffuser 134. After the absorption of the energy from the pulsed laser, the absorber layer 136 will experience a thermal expansion and create a pressure wave that is perpendicular to the ball surface. Therefore, MHz sound waves that propagate omnidirectionally will be generated. The ultrasound emitter incorporated in the guide wire assembly 104 in the present invention provides about a 260° angle acoustic emission at about 2 MPa (typical diagnostic ultrasound level), which enables a measured single-to-noise ratio (SNR) from about 38-53 dB in water.

Referring to FIG. 2b, the optical diffuser 134 sphere formed on the tip of the fiber 132. The diffuser sphere 134 can be coated around the tip of the guide wire assembly 104 and can be made up of ZnO Nano-Crystals and composite, which allow a wide angular light emission. In one exemplary embodiment, the diffuser sphere 134 can be composed by ZnO nanoparticles and epoxy and has a diameter about 600 μm. The diameter of the diffuser sphere 134 is mainly affected by the fiber 132 diameter, submerged depth and time of the fiber tip in the solution. To transform the diffused light into high-amplitude ultrasound signal, material with high optical absorption, efficient heat transduction and high thermal expansion can be used to coat the diffuser sphere.

In one exemplary embodiment, graphite, which has high optical absorption and heat transduction, and epoxy, which is easily accessible and has about three times higher thermal expansion coefficient than gold, can be mixed and applied as the outer coating on the diffuser sphere. Graphite powder can be mixed with epoxy at a concentration between about 1% to about 20%, about 10% to about 15%, or about 12.5% in solution. The fiber tip with diffuser sphere was placed in the graphite and epoxy solution with the entire sphere submerged below the surface and then quickly pulled up. Also, the fiber 132 was later vertically placed in room temperature for another 30 minutes to wait for the graphite layer to cure.

Referring to FIG. 2c, an optical absorber layer 136 coated outside of the ball-shape diffuser 134. The optical absorber 136 in the present invention can be a layer of graphite and polydimethylsiloxane (PDMS) composite that permit a large optical absorption and thermal elasticity. In one exemplary embodiment, the optoacoustic guide wire assembly 104 is shown with graphite layer coated, and the finalized size is about 831 μm.

Referring to FIG. 2d, a characterization setup for light intensity directivity map and optoacoustic signal intensity directivity map is provided. The elements are a neutral density (ND) filter 140 and a lens (L) 142. The host computer 1000 is further described in FIG. 6. The characterization of the optoacoustic wire guide is now described. A light intensity directivity map with only the diffuser sphere, and an optoacoustic signal intensity directivity map with graphite layer coated are first determined for the optoacoustic guide wire. Except for difference in the specific light source 102 and detector 144, which can be comprised of at least one ultrasound transducer. Both characterizations can share a similar setup arrangement, as shown in FIG. 2d. In one exemplary embodiment, a detector 144 having at least one transducer can be mounted on the motorized rotation stage 146 to rotate around the optoacoustic guide wire assembly 104 to detect signals at different angles. In one embodiment, a continuous He—Ne laser (632 nm) was applied as the light source, and its power was around 1 mW. To improve the signal sensitivity, a bandpass filter 140, which can be about 0.5 MHz-about 4 MHz, can be applied on the acquired optoacoustic waveform. In one exemplary embodiment, the warning distance can be set to 10 mm. If the distance detected is larger than the warning distance, a visual or audible notification is triggered to alert the user. Such a notification element can include a green light, which can be triggered to be turned on by the host computer when the assembly 104 is placed in the tissue. Alternatively, a red warning light can be displayed when a user approaches the warning zone. When scalpel is not in contact with tissue, both lights would be off to negatively notify the operator.

For integration with the scalpel 134 a miniaturized transducer 106 can be utilized with a small size about 2 mm but with a high center frequency, such as about 10 MHz, which is much higher than the center frequency of optoacoustic wave generated. By employing a compact transducer 106 with a lower center frequency or scalpel design with bigger package space for transducer, the optoacoustic signal intensity can be further improved. The experimental configurations for light intensity and optoacoustic signal intensity directivity map characterizations is repeated for further clarification. The setup for light intensity directivity map and optoacoustic signal intensity map measurement shares similar experimental schematics, which is shown in FIG. 2d, except for differences in specific light source, lens and detector 144.

For the light intensity directivity map, any suitable light source can be applied, such as a continuous 632 nm He—Ne Laser. In some exemplary embodiments, there is no neutral density filter between the laser 102 and the fiber coupling lens 142. One exemplary embodiment, can use a biconvex, having an f=35 mm. A photodiode can be fixed at a motorized rotation stage 146 with a distance of about 3 cm to the rotation center, and then used to detect the light intensity at different angles. The step size of rotation angle can be about 10 degrees. The readout of the light intensity on the photodiode can be done by using NI-scope 148 and then was transferred to the host computer 1000. As for the optoacoustic signal intensity directivity map measurement, the light source 102 can be a customized laser system, such as an OPO laser system. The OPO pumped by the second harmonic of a Nd:YAG laser can generate about 10 Hz, 5 ns pulses with wavelengths tunable from about 670 nm to about 2300 nm and with pulse energy in the range of about 60 to about 100 mJ in optoacoustic signal intensity directivity map measurement.

In one exemplary embodiment, the wavelength can be tuned to be about 1210 nm, and replaced the coupling lens 142 with an f=125 mm. A neutral density filter 140 (ND=2.0) can be placed between the lens and tip of the fiber 132, and about 0.7 mJ power can be incident on the fiber tip. The detector 144 fixed on the rotation stage 146 can be a miniaturized ultrasound transducer 106. Both optoacoustic guide wire assembly 104 and transducer 106 can be submerged in a water tank. The ultrasound radiofrequency signal read out can be done by an ultrasonic pulse/receiver and then transferred to NI-scope 148 used. The diameter of this miniaturized ultrasound transducer can be about 2 mm, and it has a center frequency at about 10 MHz and a bandwidth about 50%.

By rotating the motorized stage 146, peak-to-peak value and the waveform of the optoacoustic signal can be recorded at different angles and saved to the host computer. The experimental configurations for optoacoustic signal-to-noise ratio after passing tissue of different thickness is repeated for added clarity. These experimental configurations are illustrated in FIGS. 9a-d below.

FIG. 3a-d illustrates the design of a miniaturized transducer group 106 that can be attached to the breast tissue, an exemplary procedure of insertion of the said guide wire assembly 104 to breast lesion and an opto-electronic interface between the guide wire assembly 104 and the transducer group 106. An introducer can be used to better and more accurately insert the guide wire assembly 104, which is further detailed in FIG. 4. The transducer group 106 can include a sticky spherical mount with three transducers separated at about 30 mm distance to each other and IR reflective markers or two-dimensional barcode placed on a flat mount. The transducer group also links with an optical fiber connector 164 and electronic cable (not shown). During the procedure, the miniaturized transducer group 106 is patched to the breast tissue 122 after the guide wire assembly 104 has been placed into the lesion mass. By allowing the guide wire assembly 104 to pass through the hole in the center, the close attachment of the transducer group 106 to the breast tissue can be achieved. Then the optical fiber connector 164 that linked to transducer group 106 can be connected with the optical waveguide at the proximal end of the optical guide wire assembly 104. At the same time, the IR markers or two-dimensional barcode form a trackable rigid body for optical tracking of the transducer group 106. It is contemplated that the IR markers can be either active LED markers or passive (reflective) markers working with IR light source.

Figure 4:
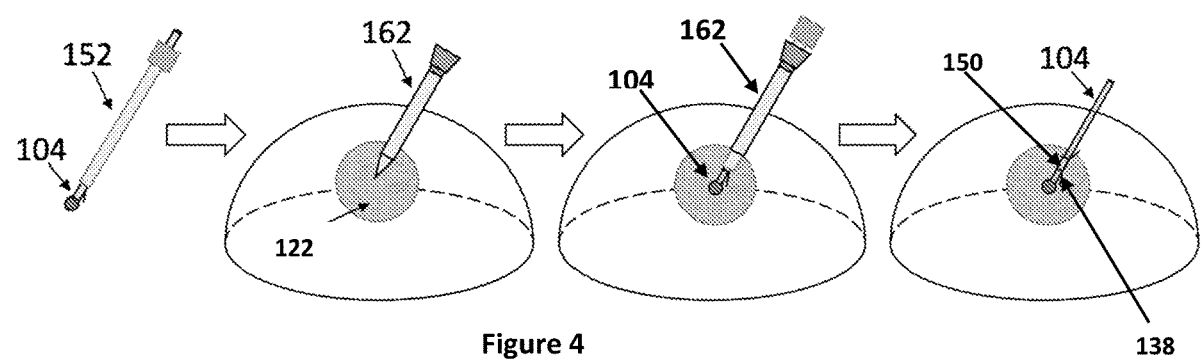
FIG. 4 is a detail diagram of an exemplary procedure of inserting and securing the optoacoustic guide wire for lesion localization

Similarly, FIG. 4 illustrate an exemplary embodiment of an assembly to insert the optoacoustic guide wire to a lesion. The assembly can comprise an introducer 162. The introducer 162 can first be punctured into the lesion mass. A guide wire with a clinical relevant needle 152 can be fed through the introducer into the lesion mass. After slowly pulling introducer and the needle 152 to release the guide wire assembly 104, guide wire assembly 104 stays alone in the lesion mass. And the hook wire 138 attached onto the guide wire assembly 104 via a heat shrink tube 150 ensures no migration will occur.

Figure 5:
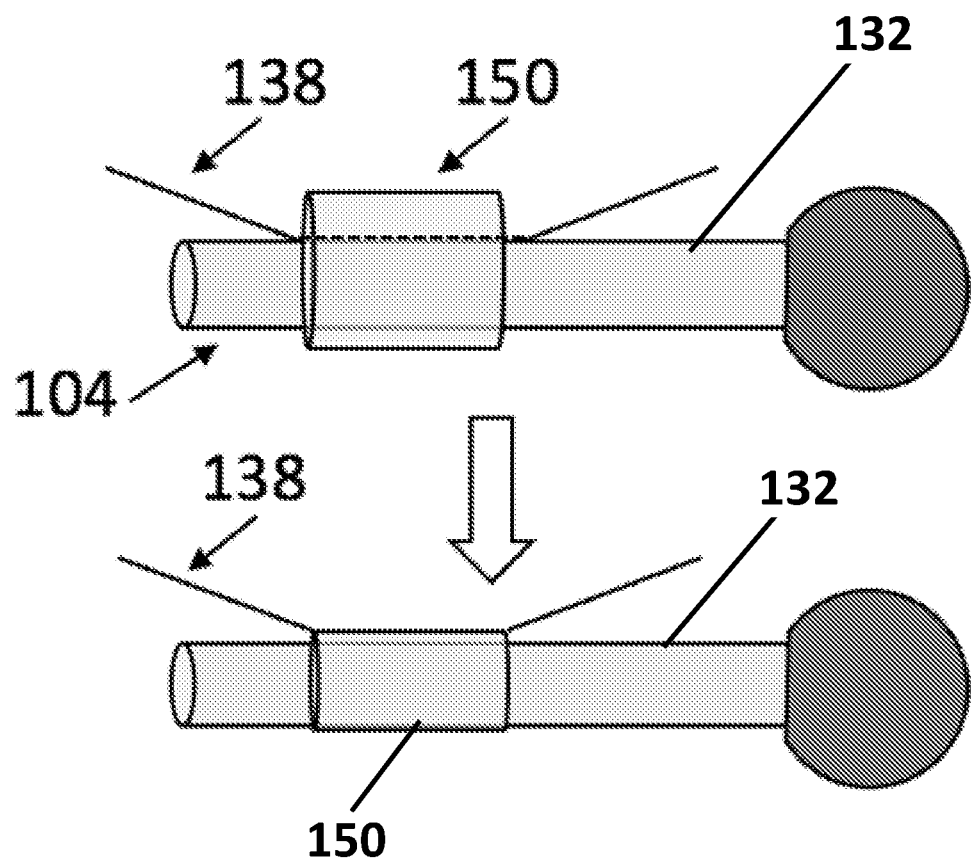
FIG. 5 is an illustration of a clinical relevant hook guide wire fabrication process in accordance with at least one embodiment of the present invention.

FIG. 5 further illustrates one exemplary fabrication process of attaching a hook wire 138 to the optical waveguide 132 of the optoacoustic guide wire assembly 104. The migration of the localization guide wire or seed during the breast conserving surgery would result in failure of initial surgical planning. To enable an easy and successful insertion and placement of guide wire in the lesion mass, a clinical relevant hook guide wire is developed to secure the position of the guide wire assembly 104 inside the tissue. First, the customized guide wire assembly 104 is fed through a 10 mm long miniature heat shrink tube 150. A hook wire 138 can also be fed through the tube, and had the unbent part aligned with the tube. The tube 150 is then properly heated to shrink and there binds the hook wire 138 with the guide wire assembly 104.

Figure 6:
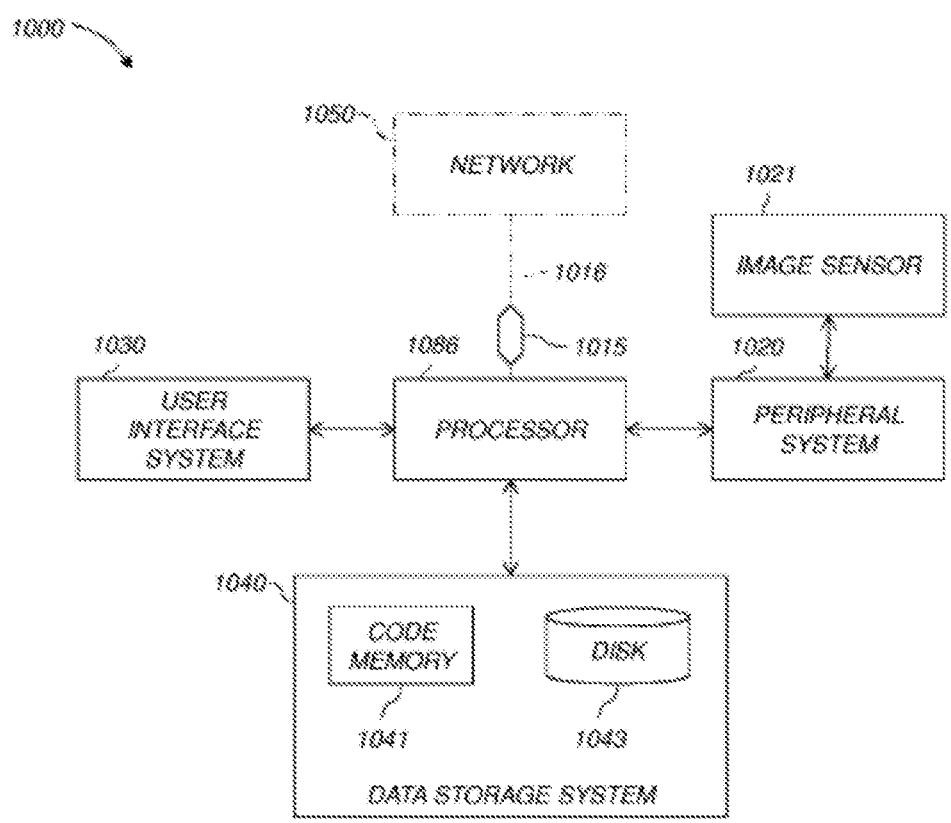
FIG. 6 is diagram showing the components of an exemplary data processing system for analyzing data and performing other analyses of lesions within a patient's tissue.

Referring to FIG. 6, a high-level diagram showing the components of an exemplary data processing system 1000 for analyzing data and performing other analyses described herein, and related components is provided. The system includes a processor 1086, a peripheral system 1020, a user interface system 1030, and a data storage system 1040. The peripheral system 1020, the user interface system 1030 and the data storage system 1040 are communicatively connected to the processor 1086. Processor 1086 can be communicatively connected to network 1050 (shown in phantom), e.g., the Internet or a leased line, as discussed below. The imaging and 3D point data described in the papers may be obtained using imaging sensors 1021 and/or displayed using display units (included in user interface system 1030) which can each include one or more of systems 1086, 1020, 1030, 1040, and can each connect to one or more network(s) 1050. Processor 1086, and other processing devices described herein, can each include one or more microprocessors, microcontrollers, field-programmable gate arrays (FPGAs), application specific integrated circuits (ASICs), programmable logic devices (PLDs), programmable logic arrays (PLAs), programmable array logic devices (PALS), or digital signal processors (DSPs).

Processor 1086 can implement processes of various aspects described herein. Processor 1086 can be or include one or more device(s) for automatically operating on data, e.g., a central processing unit (CPU), microcontroller (MCU), desktop computer, laptop computer, mainframe computer, personal digital assistant, digital camera, cellular phone, smartphone, or any other device for processing data, managing data, or handling data, whether implemented with electrical, magnetic, optical, biological components, or otherwise. Processor 1086 can include Harvard-architecture components, modified-Harvard-architecture components, or Von Neumann-architecture components.

The phrase "communicatively connected" includes any type of connection, wired or wireless, for communicating data between devices or processors. These devices or processors can be located in physical proximity or not. For example, subsystems such as peripheral system 1020, user interface system 1030, and data storage system 1040 are shown separately from the data processing system 1086 but can be stored completely or partially within the data processing system 1086.

The peripheral system 1020 can include one or more devices configured to provide digital content records to the processor 1086. For example, the peripheral system 1020 can include digital still cameras, digital video cameras, cellular phones, or other data processors. The processor 1086, upon receipt of digital content records from a device in the peripheral system 1020, can store such digital content records in the data storage system 1040.

The user interface system 1030 can include a mouse, a keyboard, another computer (connected, e.g., via a network or a null-modem cable), or any device or combination of devices from which data is input to the processor 1086. The user interface system 1030 also can include a display device, a processor-accessible memory, or any device or combination of devices to which data is output by the processor 1086. The user interface system 1030 and the data storage system 1040 can share a processor-accessible memory.

In various aspects, processor 1086 includes or is connected to communication interface 1015 that is coupled via network link 1016 (shown in phantom) to network 1050. For example, communication interface 1015 can include an integrated services digital network (ISDN) terminal adapter or a modem to communicate data via a telephone line; a network interface to communicate data via a local-area network (LAN), e.g., an Ethernet LAN, or wide-area network (WAN); or a radio to communicate data via a wireless link, e.g., WiFi or GSM. Communication interface 1015 sends and receives electrical, electromagnetic or optical signals that carry digital or analog data streams representing various types of information across network link 1016 to network 1050. Network link 1016 can be connected to network 1050 via a switch, gateway, hub, router, or other networking device.

Processor 1086 can send messages and receive data, including program code, through network 1050, network link 1016 and communication interface 1015. For example, a server can store requested code for an application program (e.g., a JAVA applet) on a tangible non-volatile computer-readable storage medium to which it is connected. The server can retrieve the code from the medium and transmit it through network 1050 to communication interface 1015. The received code can be executed by processor 1086 as it is received, or stored in data storage system 1040 for later execution.

Data storage system 1040 can include or be communicatively connected with one or more processor-accessible memories configured to store information. The memories can be, e.g., within a chassis or as parts of a distributed system. The phrase "processor-accessible memory" is intended to include any data storage device to or from which processor 1086 can transfer data (using appropriate components of peripheral system 1020), whether volatile or non-volatile; removable or fixed; electronic, magnetic, optical, chemical, mechanical, or otherwise. Exemplary processor-accessible memories include but are not limited to: registers, floppy disks, hard disks, tapes, bar codes, Compact Discs, DVDs, read-only memories (ROM), erasable programmable read-only memories (EPROM, EEPROM, or Flash), and random-access memories (RAMS). One of the processor-accessible memories in the data storage system 1040 can be a tangible non-transitory computer-readable storage medium, i.e., a non-transitory device or article of manufacture that participates in storing instructions that can be provided to processor 1086 for execution.

In an example, data storage system 1040 includes code memory 1041, e.g., a RAM, and disk 1043, e.g., a tangible computer-readable rotational storage device such as a hard drive. Computer program instructions are read into code memory 1041 from disk 1043. Processor 1086 then executes one or more sequences of the computer program instructions loaded into code memory 1041, as a result performing process steps described herein. In this way, processor 1086 carries out a computer implemented process. For example, steps of methods described herein, blocks of the flowchart illustrations or block diagrams herein, and combinations of those, can be implemented by computer program instructions. Code memory 1041 can also store data, or can store only code.

Various aspects described herein may be embodied as systems or methods. Accordingly, various aspects herein may take the form of an entirely hardware aspect, an entirely software aspect (including firmware, resident software, micro-code, etc.), or an aspect combining software and hardware aspects These aspects can all generally be referred to herein as a "service," "circuit," "circuitry," "module," or "system."

Furthermore, various aspects herein may be embodied as computer program products including computer readable program code stored on a tangible non-transitory computer readable medium. Such a medium can be manufactured as is conventional for such articles, e.g., by pressing a CD-ROM. The program code includes computer program instructions that can be loaded into processor 1086 (and possibly also other processors), to cause functions, acts, or operational steps of various aspects herein to be performed by the processor 1086 (or other processor). Computer program code for carrying out operations for various aspects described herein may be written in any combination of one or more programming language(s), and can be loaded from disk 1043 into code memory 1041 for execution. The program code may execute, e.g., entirely on processor 1086, partly on processor 1086 and partly on a remote computer connected to network 1050, or entirely on the remote computer.

One exemplary procedure using the opto-acoustic guide wire assembly to detect and image lesion. First, an internal source, such as a fiber-optic-based guide wire assembly, can be implanted into the lesion. The internal source can be used to supply energy to a patient's tissue. After activating an internal source, a detector having at least one transducer outside of the breast can triangulate the location of the internal source. In another exemplary embodiment, the internal source can be activated by coupling a pulsed laser to the fiber, the tip of the guide wire will emit acoustic waves. The surgeon can utilize an augmented reality (AR) system, in which a depth sensor will sense the position of the transducer group and will calculate the relative position of the guide wire tip to the AR display, i.e. a tablet or eye-wear glasses. The tip of the guide wire inside the lesion mass will be rendered and superimposed on the breast to provide a direct visual feedback of the lesion location, which will greatly ease the surgical planning during the operation.

This aforementioned method allows for precise lesion localization or implanted device localization with real-time visual feedback during the surgical procedure. This is accomplished by visually locating an acoustic source in a turbid media. Both an acoustic radar concept (acoustical localization) and a depth sensing technology (optical localization) are integrated to transfer the location of an acoustic source to a first-person-perspective visual source. This invention provides fast and intuitive feedback of the lesion location for surgeons. Thus it can greatly enhance the efficiency of surgical planning during operation.

Figure 7:
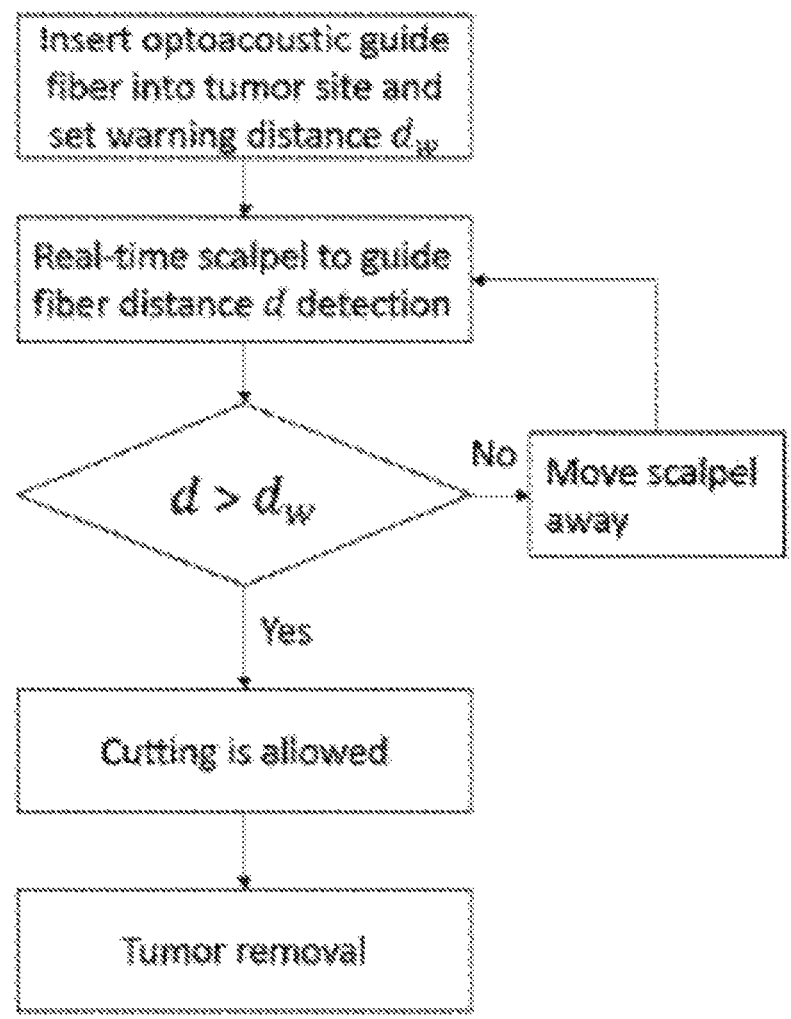
FIG. 7 is a flow chart for the process of excising a tumor or lesion from a patient's tissue.

FIG. 7 is a flow chart for the process of excising a tumor or lesion. When the distance d from a surgical blade to optoacoustic guide wire assembly is smaller than a predetermined warning distance $d_w$, a warning indicator can be triggered to inform the user that the surgeon has passed the warning distance threshold. When the surgical blade is at a distance larger than the warning distance, a safe indicator can be displayed or triggered to allow the scalpel to cut.

An optoacoustic guide fiber can first be inserted in the tumor xenograft. A miniaturized ultrasound transducer on the tip of a scalpel and a custom-built software program can display real-time distance of the scalpel to the optoacoustic guide wire assembly with visual indicators to guide the excision. More specifically, two indicator can be displayed on the user interface to inform the user of the distance of the scalpel relative to the predetermined warning distance.

Experimental Data

Figure 8:
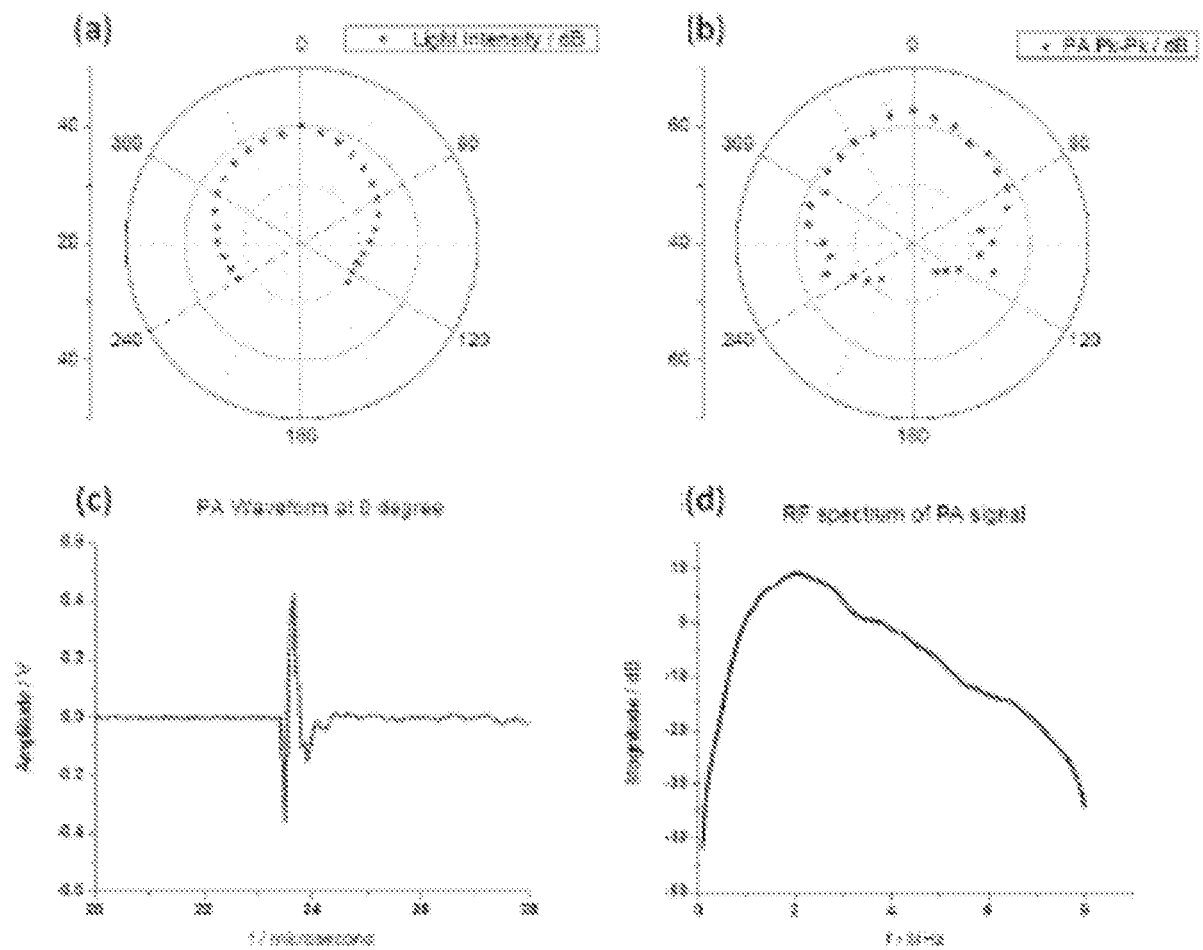
FIG. 8a is a light intensity directivity map wherein the fiber tip has a diffuser sphere.
FIG. 8b is an optoacoustic signal intensity directivity map.
FIG. 8c is a recorded optoacoustic waveform in front of the fiber tip at 0 degrees.
FIG. 8d is the radio frequency spectrum of the optoacoustic signal.

Referring to FIGS. 8a-8d, results from the characterization of the optoacoustic guide wire is provided. Referring to FIG. 8a, a light intensity directivity map (in dB) with diffuser sphere formed on the fiber tip is shown. The diffuser sphere successfully spreads the light within the apex angle of 250 in the air. The resulting illumination pattern reaches its maximum in front of the tip, and the light intensity falls off gradually as the light's direction goes backward. Noticeably, the intensity never drops about 10 dB below the maximum over the measured angular range.

The next step in characterization of the optoacoustic guide wire is the optoacoustic signal intensity directivity map. An optical parametric oscillator (OPO), can generate a nanosecond pulse at about 10 Hz, can be set to about 1210 nm wavelength to function as the excitation source for the optoacoustic guide wire. The power incident on the distal end of optoacoustic guide wire was about 0.7 mJ in experiments. A miniaturized ultrasound transducer was then used to record the ultrasound signal over an angular range about 260. Referring to FIG. 8b, the optoacoustic signal intensity (peak-to-peak value) directivity map (in dB) is shown. The measured signal intensity agrees quite well with the light intensity directivity map, shown in FIG. 8a. It also covers an angular range as wide as 260 with a drop no more than 17 dB compared to the maximum signal intensity at 0.

The difference between these two angular range coverages is a result of the difference of the measured angular range in their setups. The detector in light intensity directivity characterization was a photodiode, which has a size larger than the miniaturized transducer and makes its measurable angular range smaller than that in optoacoustic measurement. Therefore, the optoacoustic guide wire spreads the light and the optoacoustic signal within a large apex angle about 260. Referring to FIG. 8c, a recorded optoacoustic waveform in front of the fiber tip is shown. The peak-to-peak value of the waveform is about 0.783 V. After the calibration of the transducer used, the frequency spectrum of the recorded optoacoustic waveform of FIG. 8c is obtained and is shown in FIG. 8d. The spectrum shows that the spectrum spans mainly in the low frequency region and its center frequency is about 2.002 MHz. The ultrasound with such low frequency propagates inside tissue with very small attenuation compared to those high frequency ones, therefore the optoacoustic wave generated by the acoustic guide wire according to the present disclosure can penetrate very deeply into human tissue by its low-frequency nature.

Figure 9:
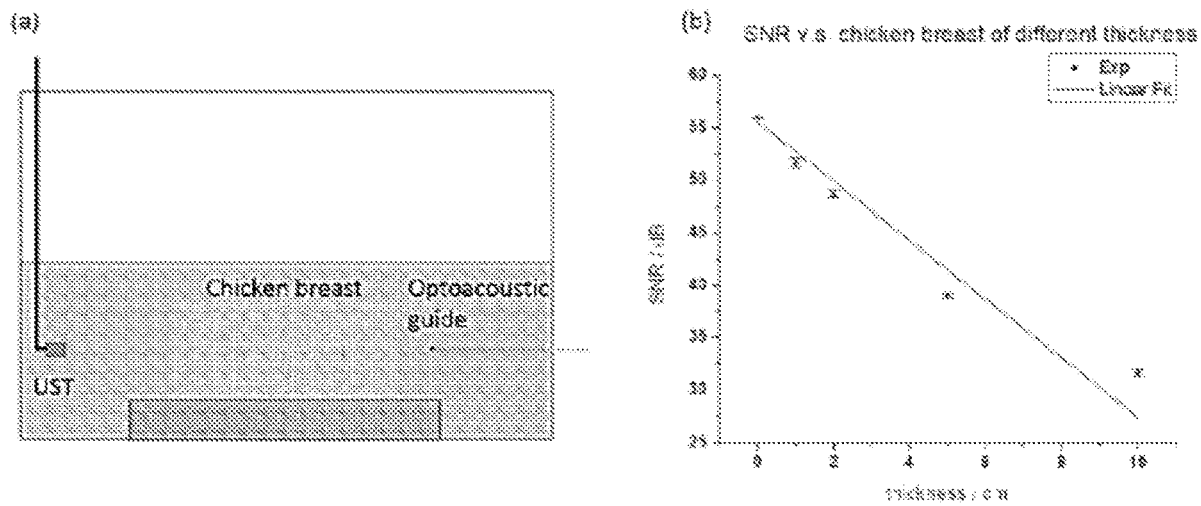
FIG. 9a is a schematic for an experimental setup to characterize the SNR passing through tissue samples.
FIG. 9b illustrates the SNR results for experiments using chicken breast as tissue.

To quantify the signal penetration depth, the signal-to-noise (SNR) of the optoacoustic waveform after passing through chicken breast tissue of different thickness was measured. The transducer was placed in front of the fiber tip, and chicken breast tissue of different thickness were placed between the transducer and the optoacoustic guide wire, as shown in FIG. 9a. FIGS. 9a-9b show a setup and results for determining SNR passing through biological tissue. FIG. 9a shows a schematic for an experimental setup to characterize SNR through chicken breast of different thickness placed between the optoacoustic guide and the ultrasound transducer (UST).

FIG. 9a shows the experimental schematic used to investigate the penetration depth of optoacoustic signal generated. The optoacoustic guide and the miniaturized ultrasound transducer were submerged in a water tank and separated by about 13 cm distance. The miniaturized ultrasound transducer was mounted on a three-axis translation stage. The same OPO laser was applied as excitation in this setup, and same power was incident on the fiber tip.

FIG. 9b shows the SNR (in dB) results for chicken breast of 1, 2, 5 and 10 cm. Without the chicken breast, the SNR was initially about 54 dB, and it almost drops linearly as the thickness of chicken breast increases. Using a linear fit (the solid line), the attenuation coefficient is estimated about 2.8 dB/cm. After passing the chicken breast of 10 cm thickness, the SNR of the optoacoustic waveform is still as high as 30 dB. Even including the 17 dB intensity drop in the most backward emission angle, the SNR would still be at least 13 dB at 10 cm distance from the optoacoustic guide wire. Such long detection distance would make the optoacoustic guide wire fit quite well in the real BCS operation, in which guide localization wire currently used is about 5-10 cm long.

To demonstrate the efficacy of optoacoustic guide wire in guiding the tumor removal, an excision demonstration of a tumor embedded in chicken breast with the optoacoustic guide wire was carried out. The present invention can be used to identify a tumor with the optoacoustic wire guide according to the present disclosure embedded in the tissue of a patient. In one exemplary embodiment of the present invention, a miniaturized ultrasound transducer can be present on the tip of a scalpel and utilizing a custom-built software program, can produce a real-time display the distance of the scalpel to the optoacoustic guide wire and visual indicators, the tumor excision can be guided. More specifically, two light indicators can be provided on the host computer monitor. As previously disclosed, when a scalpel, which can have a miniaturized ultrasound transducer on its tip is in a distance larger than a preset warning distance, an indicator light, such as a green light, can turn on. Alternatively, a warning light and/or warning sound can turn on when scalpel crosses the warning distance line. Using such method, the tumor excision using the optoacoustic guide wire according to the present disclosure can be accomplished.

When examining a patient's tissue for a lesion, the tissue is placed between the ultrasound transducer and the optoacoustic guide. Then, the ultrasound transducer is aligned with the optoacoustic guide by adjusting the three-axis translation stage to obtain the strongest optoacoustic signal. Next, the tissue of different thickness can be placed between the ultrasound transducer and the optoacoustic guide. Peak-to-peak value is recorded using a digital oscilloscope, and the noise value is recorded in the same way by turning down the OPO laser.

In one experiment using chicken breast tissue and a lesion, the demonstration of lesion excision in chicken breast using optoacoustic guide wire is repeated for further clarity. A lesion harvested from a mouse was embedded in a chicken breast. The lesion size was about 20 mm. An 18-G needle was used to pierce about 10 mm into the lesion, and guide the insertion of optoacoustic guide in the lesion. Then, the lesion and the optoacoustic guide were embedded in a chicken breast tissue. Also, the same OPO laser and same power as previous setup was applied here as the excitation source. To demonstrate the excision process as close as possible to the real practice, the miniaturized ultrasound transducer was mounted on the tip of a surgical scalpel using epoxy, and a custom-built program was developed to real-time display the distance information and warning signs if scalpel gets too close to lesion.

Figure 10:
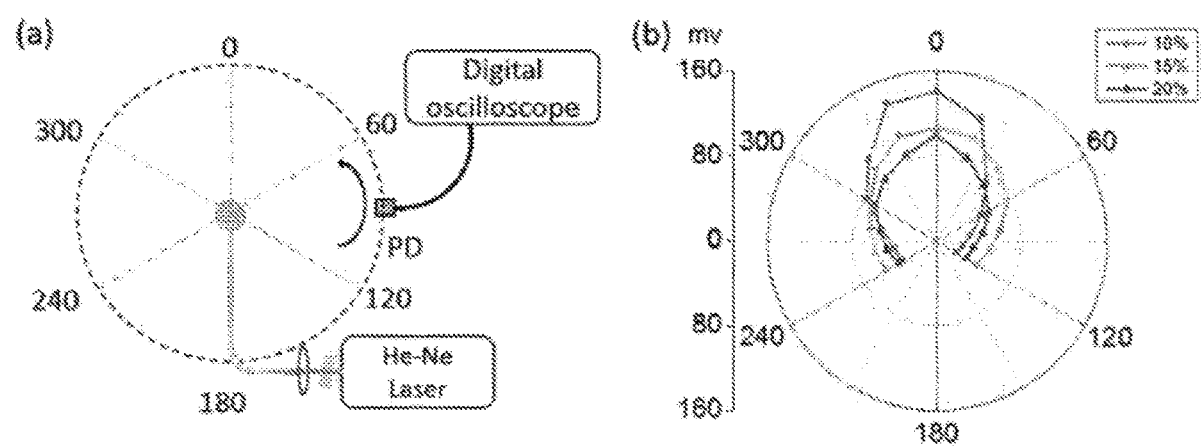
FIG. 10a illustrates the experimental setup for mapping the light intensity directivity of the optoacoustic emitter.
FIG. 10b is a light intensity directivity map of a diffuser sphere with different ZnO nanoparticle concentrations.

Referring to FIG. 10a, a continuous He—Ne laser light (about 632 nm) was coupled to the optical fiber from its distal end, and a photodiode (PD) was mounted on a motorized rotation stage to measure the light intensity over different angles. Light intensity read-out was recorded by a digital oscilloscope. FIG. 10b illustrates a light intensity directivity map of optoacoustic emitter with diffuser sphere composed of ZnO nanoparticles at different concentrations (about 10%, about 15% and about 20% by weight). The radius of data point marks its light intensity (arbitrary unit): the further out the data point lies, the higher its intensity.

Generally, the greater the number of scatters per unit volume inside the diffuser sphere, the more randomized and uniform angular light intensity distribution would be obtained. On the other hand, scatters at high concentration would result in a decrease of light intensity. To determine the optimal ZnO nanoparticle concentration inside the diffuser sphere, the light intensity directivity map of diffuser spheres was measured at three different ZnO concentrations (about 10%, about 15% and about 20% by weight). FIG. 10a shows the experimental setup for mapping the light intensity directivity of the optoacoustic emitter. A continuous He—Ne laser (about 632 nm) was coupled into the fiber, and a photodiode was mounted on a motorized stage to detect the light intensity over different angles. The experimental results of light directivity map of diffuser sphere with different ZnO nanoparticle concentrations are shown in FIG. 10b.

All diffuser spheres spread the light within an apex angle of 250 degree in the air, and their resulting emission pattern reaches their maximum in front of fiber tip and falls gradually as the light direction goes backward. The angular light intensity distribution gets more uniform as the ZnO nanoparticle concentration increases from about 10 to about 20%, but the magnitude of light intensity decreases. The diffuser sphere with about 15% ZnO nanoparticle concentration shows both a relatively high amplitude and uniform angular light distribution. Noticeably, the smallest light intensity of the backward-directed light (about 43 mV) is still more than about 40% of the maximum intensity (about 106 mV). Thus, ZnO nanoparticles of about 15% concentration were chosen for later optoacoustic emitter fiber fabrication.

It will be apparent to those skilled in the art that various modifications and variations can be made in the disclosed system and method without departing from the scope of the disclosure. Other embodiments will be apparent to those skilled in the art from consideration of the specification and practice of the various implementations disclosed herein. It is intended that the specification and examples be considered as exemplary only, with a true scope being indicated by the following claims and their equivalents.

What is claimed is:

1. A surgical localization system for use with a patient tissue excision, comprising:
   an optoacoustic guide wire assembly configured to be insertable into the patient's tissue, wherein the optoacoustic guide wire assembly comprises:
      an optical waveguide, wherein said optical waveguide has a first end and a second end; and
      an omnidirectional optoacoustic emitter formed on the first end of the optical waveguide, wherein the omnidirectional optoacoustic emitter comprises:
         a spherical nanocomposite diffuser portion configured to generate uniformly distributed light emission, and
         an absorber layer, wherein the absorber layer is formed outside and around the nanocomposite diffuser portion and is configured for an optical absorption and a thermal expansion sufficient to transform light emissions into ultrasound signal;
   a light source coupled to the second end of the optical waveguide, wherein said light source emits energy to the omnidirectional optoacoustic emitter formed at the first end of the optical waveguide, wherein said nanocomposite diffuser portion diffuses said energy and said energy is transmitted to the absorber layer wherein the absorber layer generates an omnidirectional photoacoustic signal;
   at least three transducers, wherein each transducer is configured to detect a time-of-flight of the photoacoustic signal emitted from the omnidirectional optoacoustic emitter simultaneously in response to energy emitted from the light source; and
   a computer system.

2. The system of claim 1, wherein the omnidirectional photoacoustic signal emitted at an angle greater than 180° from the omnidirectional optoacoustic emitter formed at the first end of the optical waveguide.

3. The system of claim 2, wherein the nanocomposite diffuser portion is spherical and the absorber layer is formed on an outside surface of said nanocomposite diffuser portion as a coating.

4. The system of claim 3, wherein the computer system is configured to coordinate activation of the light source and acquisition of the photoacoustic signal in order to generate a position coordinate of the first end of the optoacoustic guide wire assembly and each of the at least three transducers.

5. The system of claim 1, the light source is a pulsed laser and the nanocomposite diffuser portion is comprised of a first composite material and the absorber layer is comprised of a second composite material, wherein the first composite material and the second composite material have different compositions, wherein the first composite material comprises a plurality of nanoparticles having a diameter smaller than a wavelength of light emitted by the light source to enable Raleigh scattering of the light emitted in all directions from the omnidirectional optoacoustic emitter.

6. The system of claim 5, wherein the plurality of nanoparticles of the first composite material are ZnO nanoparticles and the first composite material further comprises an epoxy component.

7. The system of claim 5, the second composite material comprises epoxy and graphite.

8. The system of claim 5, the pulse duration of the pulsed laser ranges between 100 fs and 5 µs.

9. The system of claim 8, the repetition rate of the pulse laser ranges between 1 Hz and 20 kHz, wherein each transducer is separated from each other by at least 3 cm.

10. A method for determining the location of a lesion or device-within a patient's tissue, comprising:
    providing an optoacoustic guide wire assembly to be inserted into the patient's tissue, wherein the optoacoustic guide wire assembly comprises:
        an optical waveguide having a first end and a second end,
        an omnidirectional optoacoustic emitter formed at the first end of the optical waveguide, wherein said omnidirectional optoacoustic emitter comprises a nanocomposite diffuser portion configured to generate uniformly distributed light emission and an absorber layer formed outside and around said nanocomposite diffuser portion, and wherein the absorber layer is configured for an optical absorption and a thermal expansion sufficient to transform light emissions into ultrasound signal;
    providing a laser source to emit an energy to the nanocomposite diffuser portion of the omnidirectional optoacoustic emitter, wherein the energy is scattered and diffused omnidirectionally by the nanocomposite diffuser portion;
    generating omnidirectional photoacoustic waves by photoacoustically stimulating the absorber layer of the omnidirectional optoacoustic emitter with the scattered and diffused energy from the nanocomposite diffuser portion;
    positioning a plurality of transducers pre-determined distances from said optoacoustic guide wire assembly;
    detecting said photoacoustic waves emitted by the optoacoustic guide wire assembly by one or more of the plurality of transducers to generate acoustical localization data; and
    generating a coordinate to identify the location of the lesion or device within the patient's tissue.

11. The method of claim 10, further comprising excising the lesion using a surgical instrument using the generated coordinate.

12. The method of claim 10, wherein said omnidirectional optoacoustic emitter generates an omnidirectionally pressure wave from the absorber layer on the surface of the nanocomposite diffuser portion.

13. The method of claim 12, wherein the omnidirectionally pressure wave is emitted at an angle greater than 180 degrees from the first end of the optical waveguide.

14. A localization system for a patient, comprising:
    an optoacoustic waveguide wire assembly, comprising:
        an optical waveguide having a first end and a second end; and
        a spherical omnidirectional optical emitter formed at the first end of the optical waveguide, wherein the spherical omnidirectional optical emitter comprises a diffuser portion configured to generate uniformly distributed light emission and an absorber layer wherein an outside surface of the diffuser portion is coated by the absorber layer, and wherein the absorber layer is configured for an optical absorption and a thermal expansion sufficient to transform light emissions into ultrasound signal;
    a hook wire coupled to the optical waveguide, wherein said optoacoustic waveguide wire assembly is configured to be insertable into a patient's tissue, wherein the hook wire inhibits migration of the optoacoustic waveguide wire assembly within the patient's tissue after insertion;
    a light source coupled to the second end of the optical waveguide of the optoacoustic waveguide wire assembly, wherein said light source emits energy to the absorber layer through the diffuser portion of the spherical omnidirectional optical emitter, wherein said absorber layer generates and emits omnidirectional photoacoustic waves at an angle greater than 180°;
    a plurality of transducers configured to detect a time of flight photoacoustic signal from the photoacoustic waves emitted from the spherical omnidirectional optical emitter formed at the first end of the optical waveguide in response to activation from the light source; and
    a computer system, wherein the computer system is configured to generated acoustical localization data from the coordinate activation of the light source and acquisition of the time of flight photoacoustic signals to generate a coordinate of a lesion between the position of the first end of the optoacoustic guide wire assembly and the plurality of transducers.

15. The system of claim 14, wherein the absorber layer generates an omnidirectionally pressure wave from the diffuser surface.

16. The system of claim 14, wherein the light source is a pulsed laser.

17. The system of claim 16, wherein the pulsed laser has a pulse duration between 2 ns and 5 ns and repetition rate between 1 Hz and 20 KHz.

18. The system of claim 14, wherein one or more transducers of the plurality of transducers can be further integrated with a surgical instrument and one or more infrared markers can be coupled to the surgical instrument, wherein the infrared markers can provide the system with the relative position of the surgical instrument with regard to the first end of the optical waveguide.

19. The system of claim 18, wherein said the diffuser portion is comprised of ZnO nanoparticles and epoxy; and the absorber layer is comprised of polydimethylsiloxane ("PDMS") and graphite.

20. The system of claim 14, wherein said computer system further generates virtual images representing the coordinate of the lesion or device based on the ultrasound signal acquired by the transducer.

21. The system of claim 20, further comprising an augmented reality image system comprising:
    at least one infrared marker coupled to each of the plurality of transducers, wherein said infrared markers reflect light from a light source;

a camera to capture images of the patient's tissue;
a stereo camera, wherein the stereo camera detects and tracks reflected light from each infrared marker as optical localization data;
at least one detector outside of the patient's tissue; and
an augmented reality display device to display an augmented reality image to a user;
wherein the computer system:
  (a) controls the capture of the images of the patient,
  (b) analyzes the images, pose and position of the plurality of transducers, and the spatial location of the first end of the optical waveguide with respect to the augmented reality display device;
  (c) integrating the optical localization data and the acoustical localization data, and
  (d) generates the augmented reality image, and by overlaying the augmented reality image over a region of the images corresponding to the spatial location of the first end of the optical waveguide, wherein both the view of a lesion in the patient's tissue and the visualization of the tip of guide wire assembly are displayed real-time on the augmented reality display device.

22. The system of claim 21, wherein said augmented reality display device is a heads up display configured to display the augmented reality image in real-time to a user.

* * * * *